United States Patent
Park et al.

(10) Patent No.: US 11,172,977 B2
(45) Date of Patent: *Nov. 16, 2021

(54) MATRIX ROUTER FOR SURGICAL ABLATION

(71) Applicant: AtriCure, Inc., Mason, OH (US)

(72) Inventors: Christopher J. Park, Oregonia, OH (US); Salvatore Privitera, Mason, OH (US)

(73) Assignee: AtriCure, Inc., Mason, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/132,664

(22) Filed: Sep. 17, 2018

(65) Prior Publication Data
US 2019/0175246 A1   Jun. 13, 2019

Related U.S. Application Data

(63) Continuation of application No. 14/071,234, filed on Nov. 4, 2013, now Pat. No. 10,076,378, which is a
(Continued)

(51) Int. Cl.
*A61B 18/12* (2006.01)
*A61B 18/14* (2006.01)
(Continued)

(52) U.S. Cl.
CPC .......... *A61B 18/1206* (2013.01); *A61B 5/318* (2021.01); *A61B 18/1445* (2013.01); *A61B 18/1447* (2013.01); *A61B 18/18* (2013.01);
*A61B 2018/00702* (2013.01); *A61B 2018/00791* (2013.01); *A61B 2018/00875* (2013.01);
(Continued)

(58) Field of Classification Search
CPC ........... A61B 2018/00172; A61B 2018/00178; A61B 2018/00636; A61B 2018/00642; A61B 2018/00654; A61B 2018/00726; A61B 2018/00773; A61B 2018/00875; A61B 18/124; A61B 18/126
See application file for complete search history.

(56) References Cited

U.S. PATENT DOCUMENTS 5,157,603 A * 10/1992 Scheller ................. A61B 17/32
                                                       604/22
5,342,356 A *  8/1994 Ellman .................. A61B 18/14
                                                       606/32

(Continued)

*Primary Examiner* — Ronald Hupczey, Jr.
(74) *Attorney, Agent, or Firm* — Dorton & Willis, LLP; Ryan Willis

(57) ABSTRACT

A matrix router with frequency switching is provided having an energy source electrically connected to a plurality of interface ports. A switching device is provided between the energy source and the plurality of switches. One of the plurality of interface ports includes a paired electrode interface port for the connection of a paired electrode device thereto. The paired electrode device has a first pair of opposed electrodes and a second pair of opposed electrodes for clamping on tissue. When the paired electrode device is operably connected to the paired electrode interface port and actuated, the switching device alternates energy such as bipolar RF from the first pair of opposed electrodes to the second pair of opposed electrodes.

20 Claims, 9 Drawing Sheets

Related U.S. Application Data continuation of application No. 11/969,977, filed on Jan. 7, 2008, now Pat. No. 8,603,083, which is a continuation-in-part of application No. 11/457,531, filed on Jul. 14, 2006, now abandoned.

(60) Provisional application No. 60/699,664, filed on Jul. 15, 2005, provisional application No. 60/884,783, filed on Jan. 12, 2007, provisional application No. 60/884,719, filed on Jan. 12, 2007, provisional application No. 60/973,552, filed on Sep. 19, 2007.

(51) Int. Cl.
*A61B 18/18* (2006.01)
*A61B 18/00* (2006.01)
*A61B 5/318* (2021.01)

(52) U.S. Cl.
CPC ... *A61B 2018/124* (2013.01); *A61B 2018/145* (2013.01); *A61B 2018/1432* (2013.01); *A61B 2018/1467* (2013.01)

(56) References Cited

U.S. PATENT DOCUMENTS

| | | | | |
|---|---|---|---|---|
| 5,688,235 A * | 11/1997 | Sakurai | ............ | A61B 17/22012 604/22 |
| 6,152,923 A * | 11/2000 | Ryan | ................... | A61B 18/1445 606/51 |
| 7,041,095 B2 * | 5/2006 | Wang | ................... | A61B 18/1445 606/32 |
| 7,367,974 B2 * | 5/2008 | Haemmerich | ..... | A61B 18/1477 128/898 |
| 8,603,083 B2 * | 12/2013 | Park | ................... | A61B 18/1206 606/34 |
| 10,076,378 B2 * | 9/2018 | Park | ................... | A61B 18/1206 |

\* cited by examiner

MATRIX ROUTER FOR SURGICAL ABLATION

CROSS REFERENCE TO RELATED APPLICATIONS

This application is a continuation of U.S. Nonprovisional application Ser. No. 14/071,234, now U.S. Pat. No. 10,076, 378, which is a continuation of U.S. Nonprovisional application Ser. No. 11/969,977, now U.S. Pat. No. 8,603,083, which is a continuation in part of U.S. Nonprovisional application Ser. No. 11/457,531, now abandoned, which claimed priority to and the benefit of U.S. Provisional Applications Nos., 60/884,719 filed on Jan. 12, 2007, 60/884,783 filed on Jan. 12, 2007, and 60/973,552, filed Sep. 19, 2007, and U.S. Provisional Application No. 60/699,664 filed Jul. 16, 2005. All of the above are hereby incorporated by reference in their entirety.

BACKGROUND OF THE INVENTION

The present invention relates to medical/surgical instruments and systems employing RF energy and/or monitoring or pacing devices and systems and the use thereof. In a variety of medical procedures, it may be desired to remove or cause the destruction of tissue, such as by ablation. Some examples of such procedures include, without limitation, electrical isolation of cardiac tissue to treat atrial fibrillation, ablation of uterine tissue associated with endometriosis, ablation of esophageal tissue associated with Barrett's esophagus, ablation of cancerous liver tissue, and the like. The foregoing examples are merely illustrative and not exhaustive.

In a number of the procedures in which tissue is ablated, it may be desirable to have a sensing and/or pulse generating capability. For example, when ablating cardiac tissue to control or treat atrial fibrillation, it may be desired to apply electrical pulses to the cardiac tissue or to sense for the presence of electrical signals to determine, for example, where the ablation should be carried out or whether the ablation has been successful or fully transmural (completely throughout the thickness of the tissue treated).

Because of the variety of functionalities of the devices that may be used in performing surgical ablation, a controller or "matrix router" may be advantageously used in the system to control the delivery of RF energy and/or other electrical signals to the ablation instrument.

While a variety of techniques and devices have been used to ablate or cause lesions in tissue, and/or to sense or provide pulse generating capability, the present invention provides a unique and non-obvious advance over prior devices and systems and offers unique utility not previously known or obvious.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which various aspects and embodiments of the present invention are illustrated:

DETAILED DESCRIPTION OF THE INVENTION

Figure 1:
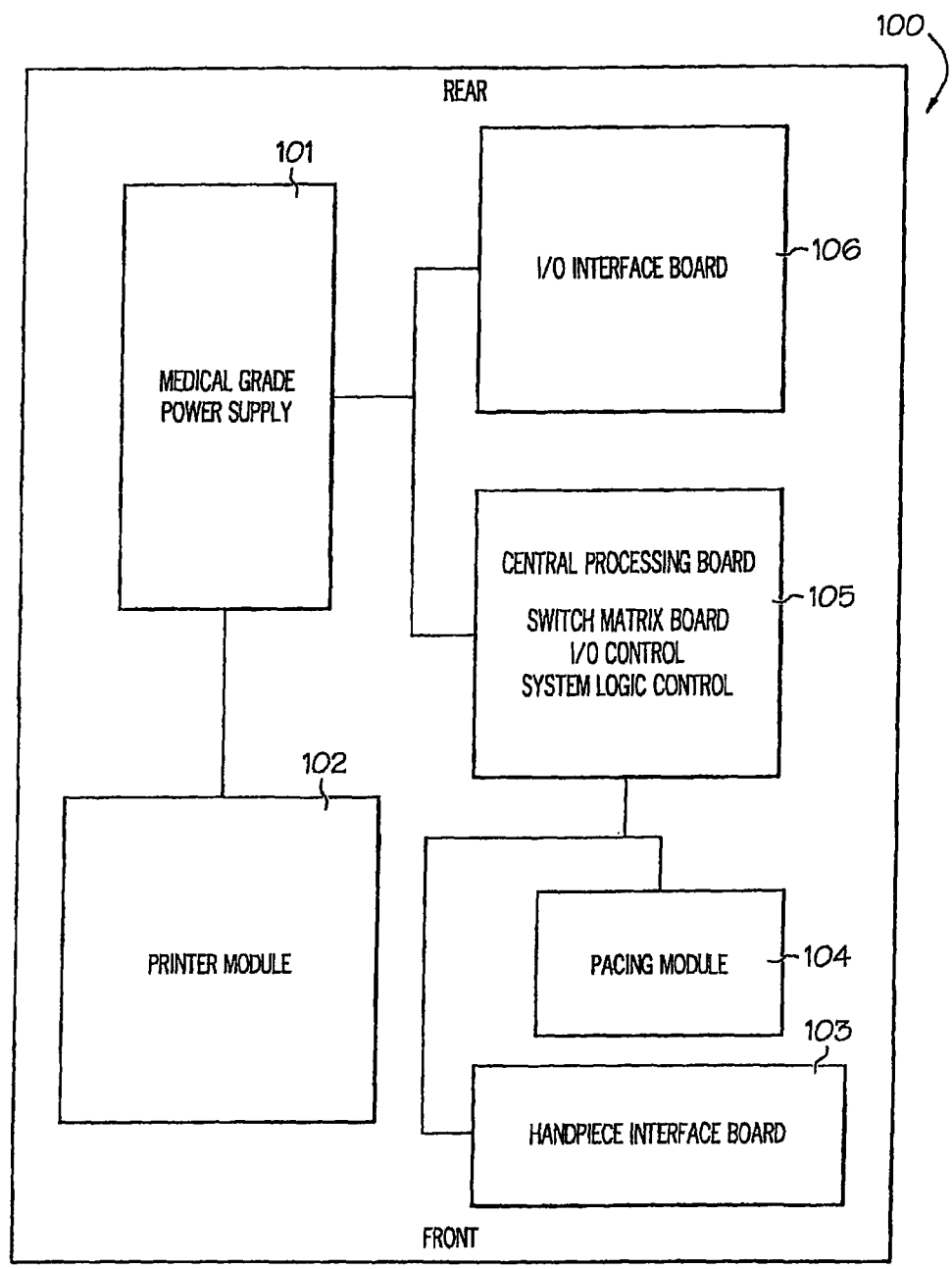
FIG. 1 is a schematic view of modules in an exemplary embodiment of a matrix router.

The following description of the accompanying drawings are for description purposes only and should not be used to limit the scope of the present invention as set forth in the claims now or hereafter filed. Other examples, features, aspects, embodiments, and advantages of the invention will become apparent to those skilled in the art from the following description, which is by way of illustration, one of the best modes contemplated for carrying out the invention. Accordingly, the drawings and descriptions should be regarded as illustrative in nature and not restrictive.

In some embodiments, a matrix router as described herein, might be used to facilitate the performance of the Maze procedure through bipolar radio frequency (RF) ablation. As is well known to one of ordinary skill in the art, the Maze procedure is a procedure used to treat atrial fibrillation, a form of cardiac arrhythmia characterized by a loss of synchrony between the atria and ventricles of the heart. The Maze procedure treats atrial fibrillation through establishing conduction blocks in the heart which serve to stop the formation and conduction of the electrical patterns which are responsible for atrial fibrillation. When using bipolar radio frequency ablation to create the conduction blocks, a surgeon uses a device, such as a transpolar (or bipolar) pen (one type of which is disclosed in a U.S. patent application Ser. No. 11/363,707 entitled "Surgical Ablation and Pacing Device" filed Feb. 28, 2006, which is incorporated by reference, by way of example only), a transpolar (or bipolar) clamp (one type of which is disclosed in U.S. Pat. No. 6,517,536, which is incorporated by reference, by way of example only), or some other surgical device, to deliver bipolar radio frequency energy to cardiac tissue.

As bipolar radio frequency energy is applied to tissue, the outer layers of the tissue may become non-conductive. As the outer layers of the tissue become non-conductive, the bipolar radio frequency energy may begin to pass through deeper and deeper levels of tissue, until eventually the entire area of tissue selected by the surgeon has been ablated, creating a conduction block. Finally, to ensure that a conduction block has been successfully created, the surgeon might test the electrical activity and response of the cardiac tissue using techniques such as pacing, stimulating and sensing. As is well known to those of skill in the art, in this context, pacing refers to applying electrical impulses to cardiac tissue at a rate higher than the patient's current heart rate (e.g., 10 to 20 beats per minute higher), stimulating refers to pacing which is performed at a relatively high rate and sensing refers to the process of monitoring the electrical activity of tissue.

As an example of the use of the above techniques, a surgeon might pace the tissue on the side of a conduction block which is opposite the heart chamber and observe the heart (for example, through visual observation, through observation of a electrocardiogram (ECG), or through some other means) to ensure that the pacing does not change the rate of the patient's heart beat. As an example of the use of sensing, a surgeon might use a tool such as an electrical sensor, to sense the electrical activity of a patient's cardiac tissue to ensure that a fibrillatory signal does not cross over a lesion formed by ablation. As an example of stimulating, a surgeon might stimulate cardiac tissue and then observe the vagal (heart rate) response on an ECG. Of course, one or more of those techniques, or other techniques known to those of skill in the art, might be combined in order to verify that a conduction block has been created. Additionally, it will be appreciated that this disclosure does not individually specify each testing technique that can be used, and will describe the use of a matrix router in terms of particular techniques, such as pacing or sensing. As will be clear to one of ordinary skill in the art, the invention is not limited to the use of the techniques specifically set forth in the description, and other techniques could be substituted for the techniques mentioned, without departing from the scope or spirit of the invention.

Because multiple pieces of equipment might be required for performing a Maze or other procedure, and those pieces of equipment might use different radio frequency energy, or might use alternative types of energy entirely, it may be desirable for a piece of equipment, such as any of the matrix routers described herein, to allow the Integration of surgical devices and to allow multiple disposable devices to be driven by a single piece of capital equipment without switching connections between devices. Further, one with ordinary skill in the art will recognize that a matrix router may be utilized in contexts other than performance of the Maze procedure, such as ablation of uterine tissue associated with endometriosis, ablation of esophageal tissue associated with Barrett's esophagus, ablation of cancerous liver tissue, and other procedures. Additionally, while the illustrative examples set forth below will generally discuss the performance of surgical procedures using bipolar radio frequency energy, it will be immediately apparent to one of ordinary skill in the art that a matrix router may be used with other types of energy, such as ultrasonic energy, mono-polar radio frequency energy, microwave energy, laser energy, or other types of energy. Further, while the description of the Maze procedure set forth above specifically mentions the use of certain tools such as a transpolar pen and a transpolar clamp, one of ordinary skill in the art will immediately recognize that other ablation surgical devices might be used to perform the Maze procedure or other surgical procedures. Therefore, the examples presented herein discussing the use of a matrix router are intended to be illustrative only, and are not intended as limiting on the scope of uses or configurations of the matrix router.

As schematically shown in FIG. 1, the matrix router (100) of the present example comprises an energy generator (101), a printer control module (102), a handpiece interface circuit (103), a pacing module (104), a control circuit (105), and an input/output circuit (106). As used herein, the term "circuit" and variations thereof should be understood to refer any type of electrical equipment, including programmable memory and associated devices. Similarly, the term module should be understood to refer to any portion of a device which performs at least one delimited function, and possibly other functions. It will be immediately apparent to one of ordinary skill in the art that a module might be implemented in circuitry, and that a single circuitry might contain multiple modules. One example of a circuitry which contains multiple modules would be a circuitry comprising memory containing multiple sets of computer instructions wherein each set of computer instructions is dedicated to accomplishing a delimited function. Other module examples will be apparent to those of ordinary skill in theart.

For purposes of illustration, a discussion of how various components and modules schematically depicted in FIG. 1 might operate and/or interact with one another will be set forth. It should be understood that such discussion is intended to be illustrative only of how certain embodiments might function, and is not intended to be limiting on the scope of the invention as a whole. In some embodiments, if a surgeon indicates a desire to use a transpolar pen with the matrix router (100) of this example, the handpiece interface board (103) will send a signal to the central processing board (105) notifying the central processing board (105) that the surgeon wishes to use a transpolar pen in a particular mode, for example, ablation mode. In response to receiving that signal, the central processing board (105) triggers the energy generator (101) or some external generator (not shown) to supply bi-polar radio frequency energy, which is then routed to the transpolar pen by the central processing board (105) through the handpiece interface board (103). When the surgeon finishes using the transpolar pen for ablation, he or she might wish to verify the creation of a conduction block, which might be done by pacing. The matrix router {100) could facilitate the process of switching from ablation to pacing through a process comprising the step of sending a signal from the handpiece interface board (103) to the central processing board (105), indicating that the transpolar pen should be used in pacing mode, rather than ablation mode. In response to receiving that signal, the central processing board {105) activates the pacing module (104), and additionally causes a connection between the pacing module (104) and the transpolar pen to be established, so that the surgeon could test to verify the establishment of a conduction block. It should be understood that, in the context of this example, establishing a connection refers to establishing a logical connection over which signals can travel, and does not necessarily refer to the creation of an actual physical connection through the installation of wires between the pacing module (104) and the transpolar pen, though in some embodiments such a physical connection might be created, e.g., by closing a switch. Once the surgeon had completed pacing, a signal is sent from the pacing module (104) to the central processing board (105) indicating that the procedure was complete. The central processing board (105) then causes the printer module (102) to create hard copy documentation of the procedure which had just been completed. Additionally, the central processing board (105) can use the input/output interface board (106) to send information related to the procedure to some networked storage facility, including local mass storage media for data retrieval.

Figure 1A:
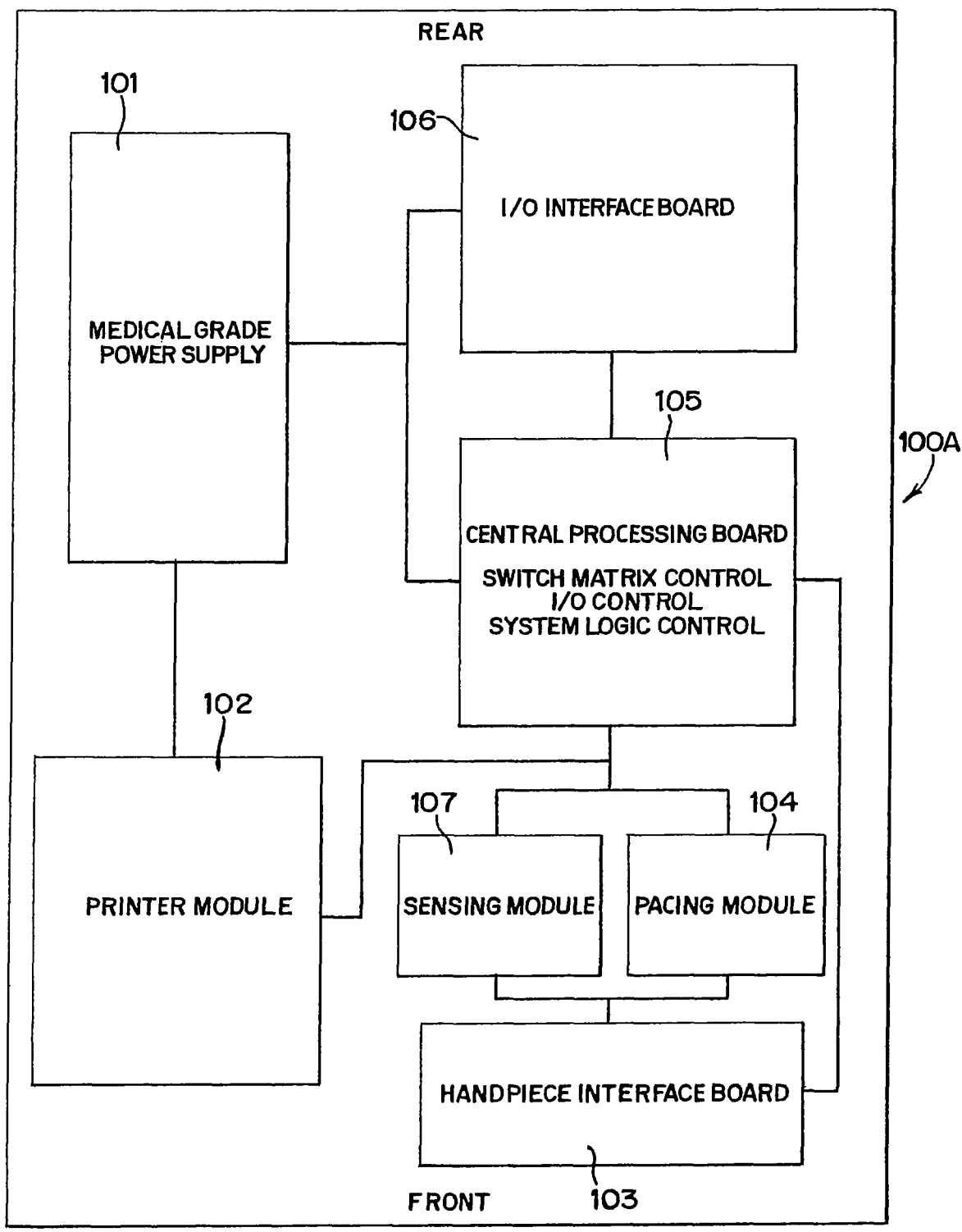
FIG. 1A is a schematic view of modules in an alternate exemplary embodiment of a matrix router.

FIG. 1A is a schematic diagram of an alternate matrix router (100A) which departs from the example of FIG. 1 by utilizing alternate connections between modules (e.g., a direct connection between the central processing board (105) and the printer module (102), instead of only having those modules connected indirectly through the energy generator (101) as was the case in FIG. 1. FIG. 1A also departs from the example of FIG. 1 by incorporating a dedicated sensing module (107) in addition to the pacing module (104) depicted in FIG. 1. It will be appreciated that such a sensing module (107) may, among other things, analyze signals obtained through a device (e.g., an ablation pen) coupled with the matrix router (100) to determine whether fibrillatory signals are crossing over a lesion and/or to provide an indication as to whether the same is occurring. As will be clear to one of ordinary skill in the art, various other combinations and configurations of modules beyond those depicted in FIGS. 1 and 1A could be incorporated into a matrix router (100) without departing from the scope of spirit of the invention.

Figure 2A:
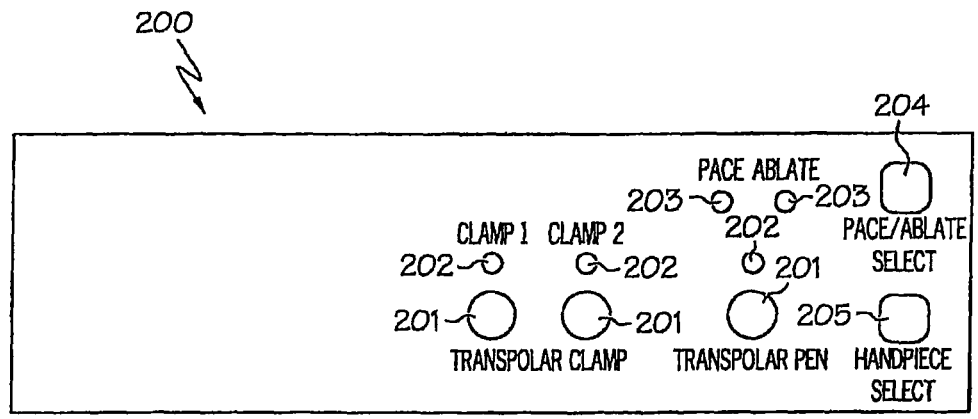
FIG. 2A illustrates a front panel of an exemplary matrix router.
Figure 2B:
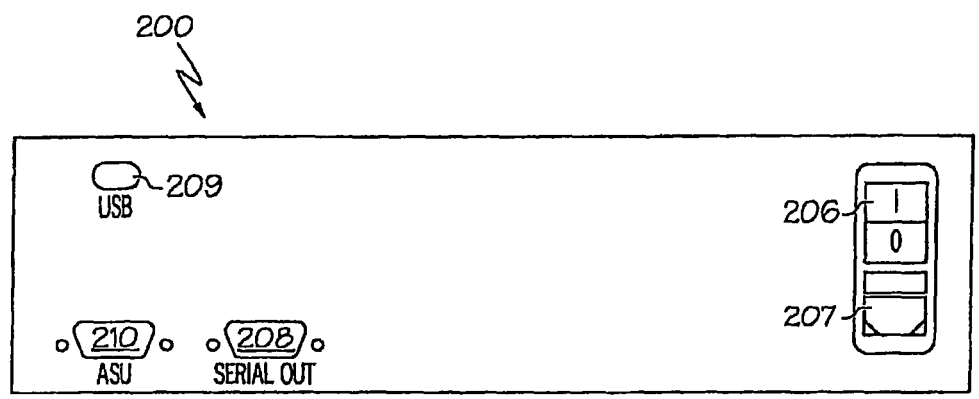
FIG. 2B illustrates a rear panel of the matrix router of FIG. 2A.

FIGS. 2A and 2B illustrate the front and rear panels, respectively, of an exemplary matrix router (200). The front of the matrix router (200) could be used by an operator, even an operator wearing typical surgical garb such as gloves, to switch between different handpieces (which might be disposable devices), and different functions, without necessarily having to change handpiece connectors or utilize multiple pieces of capital equipment. The front of the matrix router (200) shown in FIG. 2A comprises multiple interface ports (201) which may be used to establish connections with disposable devices such as a transpolar clamp, a transpolar pen, or any other device. An interface port should be understood to include a location where a connection between one or more devices and/or their constituent components can be established to allow electrical or other signals (e.g., electric current) to pass to or from, or both, the device and/or their components. The matrix router (200) shown in FIG. 2A further comprises activity lights (202) over each interface port (201) which can be used to indicate whether that interface port (201) is currently active and/or for other purposes. In addition to the activity lights (202) over the interface ports (201), the matrix router (200) further comprises mode lights (203), which can be used to indicate whether a device is currently operable in ablate or pace mode, though additional modes (e.g., stimulation mode, sensing mode, etc.) with corresponding mode lights might be utilized in some embodiments. The matrix router (200) further comprises an interface button (205) and a mode button (204) which can be used to change which interface port (201) is active, or which mode a device is to be used in, respectively. An interface port (201) which is active should be understood to mean an interface port (201) which is receiving or transmitting a signal from or to the matrix router (200). For example, if the interface button (205) was used to establish a connection between an energy generator and a first interface port (201), such that energy is being transmitted to a device through the first interface port (201), the first interface port (201) would be said to be active.

In one exemplary use, the matrix router (200) is coupled with a transpolar pen to perform the Maze procedure. Initially, the surgeon could start by pressing the interface button (205) until the activity light (202) over the interface port (201) for the transpolar pen is lit. Next, the surgeon could press the mode button (204) until the mode light (203) indicates that the transpolar pen is ready for use in ablation mode. Those lights (202, 203) being lit may signify that there is a connection between an energy generator generating bipolar radio frequency energy and the transpolar pen, and that the pen may therefore be used in ablation mode. Referring to the schematic of FIG. 1, this may be accomplished internally by circuitry comprising the handpiece interface circuit (103), sending a signal to the control circuit (105), requesting a connection be established between the appropriate interface port (201) and an energy generator for generating bipolar radio frequency energy, which might be the energy generator (101), or might be some external generator or other energy source (not shown in FIG. 1). Alternatively, a matrix router (200) could be implemented as a mechanical device wherein the interface of FIG. 2A would establish connections between handpieces and the appropriate energy generators, and the matrix router (200) would remain passive, acting only as a pass-through for signals between the energy generators and handpieces. Further, some embodiments might function using a combination of circuitry and mechanical switches.

While the surgeon is using a transpolar pen to ablate cardiac tissue, the actual amount of bipolar radio frequency energy delivered by the pen can be controlled by operational logic circuitry in the control circuit (105) which can deliver a trigger signal to the energy generator (101) to determine a power generation curve to follow as appropriate for the active device (various power generation curves and methods for selecting them are disclosed in U.S. patent application Ser. No. 11/037,810, filed Jan. 18, 2005, the teaching of which is incorporated by reference herein), or by some external RF generator (not shown). As used herein, an operational logic circuitry should be understood to mean circuitry which specifies one or more outputs on the basis of one or more given inputs. Alternatively, the device being used to ablate tissue, in this case a transpolar pen, can itself generate an identification signal indicating an appropriate power generation curve, that signal being translated through the matrix router (200) to the energy generator (101) or some external RF generator, in which case the matrix router (200) might act as a simple pass-through. In some embodiments, an energy generator (101) or an external RF generator can include various operational logic circuitries which would supply power for an appropriate power generation curve, the power generation curve being determined by the identification signal. For example, there can be two defined power generation curves, in which case the energy generator (101) or an external RF generator could contain two operational logic circuitries, one for each power generation curve. Other suitable configurations will be apparent to those of ordinary skill in the art.

Once the surgeon has finished creating a conduction block, he or she might use the pacing module (104), sensing module (107), or other modules which can be incorporated into the matrix router (200) to verify that the tissue making up the block could not transmit electrical signals introduced by pacing the tissue. The matrix router (200) facilitates this switching from ablation to pacing through the use of the mode button (204). Specifically, when the surgeon has finished ablation, he or she simply presses the mode button (204), or requests that an assistant press the mode button (204), and the matrix router (200) will switch the transpolar pen from ablation mode to pacing mode. The matrix router (200) as shown in FIG. 2A provides visual confirmation that the transpolar pen was in the proper mode by extinguishing the mode light (202) indicating ablation, and illuminating the mode light (202) indicating pacing. Referring to the schematic of FIG. 1, mode switching can be accomplished internally by the handpiece interface board (103) establishing a connection between the isolator transpolar pen and the pacing module (104), which would provide electrical signals to stimulate the cardiac tissue, and may further analyze the response detected by the transpolar pen. Additionally, the handpiece interface board (103) or pacing module (104) could also command the control circuit (105) to establish a connection between some external pacing module (not shown in FIG. 1), and the handpiece interface board (103).

While the front side of the matrix router (200) can be used to provide an interface for a surgeon to switch between different devices and different modes, the back of the matrix router (200), as shown in FIG. 2B, could be utilized for other purposes. For instance, the back of the matrix router (200) of this example has an on/off switch (206), together with an input (207) for connecting the matrix router with an external energy source (e.g., a standard wall outlet). The matrix router (200) of this example further comprises a serial input/output port (208) and a USB input/output port (209) (though some embodiments might include multiple serial input/output and/or USB input/output ports) which could be used for data transmission, connecting additional devices, or other purposes. The functionality of those components could be useful for surgery, for example to transmit reports of the procedure, or to create data archives. The matrix router (200) further comprises an interface (210) for an ablation and sensing unit (ASU), which is a piece of capital equipment capable of producing or regulating energy for ablation of tissue and might additionally include operational logic circuitries for following specific output functions for power generation, or provide sensing of various electrical parameters, among other features.

While FIGS. 1, 2A, and 2B depict a schematic of the internal workings and interfaces of an exemplary matrix router (200), those figures are intended to be illustrative only, and numerous modifications and variations of the matrix router (200) will be immediately apparent to one of skill in the art. For example, while the example of using a matrix router (200) to facilitate performance of the Maze procedure included a surgeon switching between handpieces using an interface button (205), other embodiments might expand on the handpiece interface circuit (103) of FIG. 1 to enable the matrix router (200) to automatically detect what device is being used by a surgeon, and establish a connection between that device and the appropriate capital equipment (such as the ASU) without needing to be directed by a surgeon using an interface button (205). For instance, the handpiece interface circuit (103) may automatically detect the coupling of a device to any interface port (201) and/or detect the type of device coupled to an interface port (201). Further, it will be appreciated that any other types of data connection may be provided in addition to or in lieu of the serial input/output port (208) and the USB input/output port (209) depicted in FIG. 2B. For example, in addition to, or as an alternative to, the ports (208, 209, 210) depicted in FIG. 28, a matrix router (200) might have a firewire communications port or a port for a mass storage device such as a flash memory element as well as a wireless communication media. It will be apparent to one of ordinary skill in the art that such ports may be added to the matrix router without departing from the spirit or scope of the invention. Other variations will be apparent to those of ordinary skill in the art.

Figure 3A:
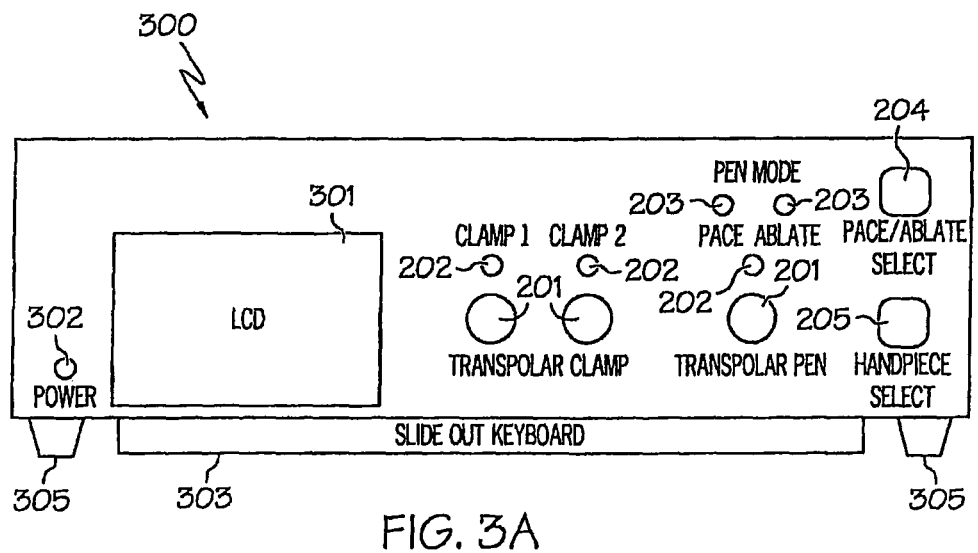
FIG. 3A illustrates a front view of a first alternative matrix router.
Figure 3B:
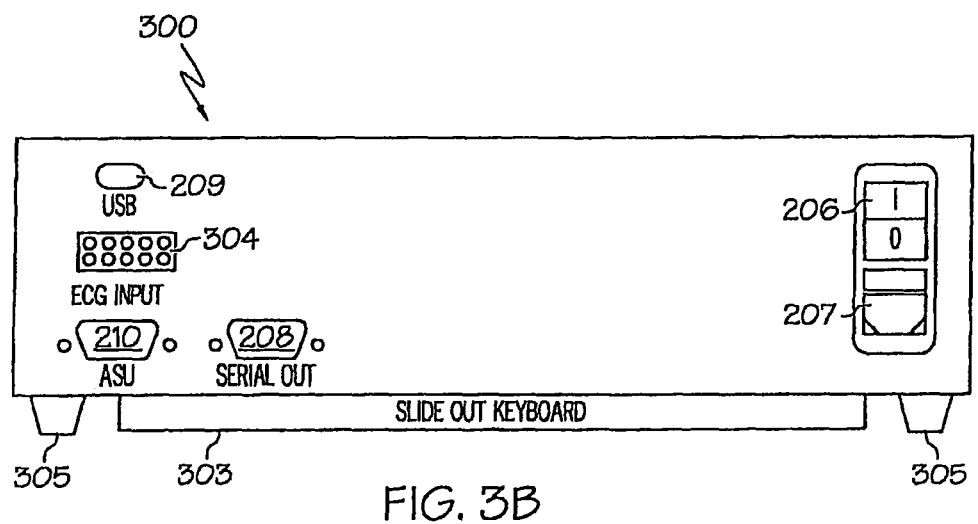
FIG. 3B illustrates a rear view of the matrix router of FIG. 3A.

FIGS. 3A and 3B show an alternative matrix router (300). In this example, all the components shown in FIGS. 2A and 2B are present, but additional components, such as a liquid crystal display (LCD) screen (301), a power indicator (302), a keyboard (303), and an input (304) for an ECG and/or esophageal probe or other type of diagnostic or other type of device have been added. In order to illustrate the use of these additional components, consider again the scenario of a surgeon performing the Maze procedure. Using the matrix router (300) the surgeon could follow the procedure outlined above for FIGS. 2A and 2B, but could additionally utilize an ECG, through the input (304) for monitoring the patient's heartbeat to ensure that the procedure was successful. Additionally, the surgeon could use the LCD screen (301) to monitor the ECG, avoiding the necessity of having a separate piece of display equipment. The slide out keyboard (303) would allow the surgeon (or an assistant, as appropriate), to input data such as patient demographics and/or physical characteristics into the matrix router (300). These additional data sources, the keyboard (303) and the input (304) may allow a more complete picture of the operation to be created, which could be archived using the serial input/output port (208) or the USB input/output port (209). The entered information can also be printed and hardcopy made available for patient record. Additionally, the keyboard (303) might be used for system configuration or other purposes, while the LCD screen (301) could be used for data presentation, in addition to simply displaying the ECG output. The power indicator (302) of this example comprises a light that is illuminated when the matrix router (300) is drawing power from an energy source (not shown). Matrix router (300) further comprises legs (305) which would allow the matrix router (300) to be placed on top of another piece of equipment, such as an ASU, without interfering with the use of the slide out keyboard (303).

As with FIGS. 1, 1A, 2A, and 28, FIGS. 3A and 3B are intended to be illustrative only of certain components which could be added to a matrix router (300) in addition to those shown in FIGS. 2A and 28. Various modifications and alterations to the components shown in FIGS. 3A and 3B will be immediately apparent to one of ordinary skill in the art. For example, the LCD screen (301) of FIG. 3A could be replaced with an alternative display technology, such as a cathode ray tube (CRT) monitor, or a plasma screen monitor, or could even be moved out of the matrix router all together, and replaced with a connection to an external graphic display device. Similarly, it will be immediately apparent to one of ordinary skill in the art that, instead of having an input to an external ECG or other diagnostic device (304), an internal ECG or other diagnostic device could be integrated into the matrix router itself. Thus, it should be understood that FIGS. 3A and 3B, like the figures which preceded them, are intended to be illustrative only, and not limiting.

Figure 4A:
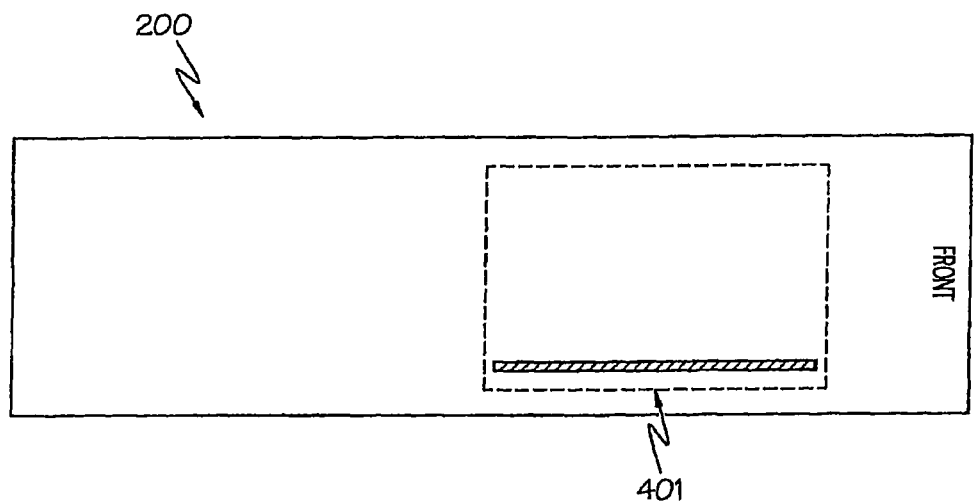
FIG. 4A illustrates a left side panel of the matrix router of FIG. 2A.
Figure 4B:
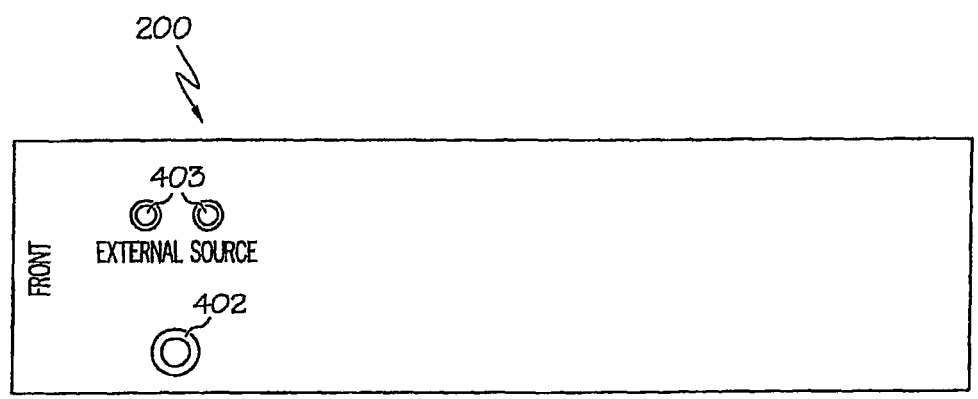
FIG. 4B illustrates a right side panel of the matrix router of FIG. 2A.

FIGS. 4A and 4B illustrate side views of the exemplary matrix router (200) of FIGS. 2A and 2B, with FIG. 4A illustrating a left view, and FIG. 48 illustrating a right view. In this embodiment, the sides of the matrix router (200) are used for input and output ports. For example, the left view of FIG. 4A includes a printer module (401), which could be a thermal printer or other type of printer integrated with the matrix router (200). The printer module (401) could be used to provide hard copy confirmation and documentation of procedures which were performed utilizing the matrix router (200). Other information suitable for printing by printer module (401) will be apparent to those of ordinary skill in the art. In the right view of FIG. 4B, there is both an interface (402) for a cable connected to an ASU or other device, and ports (403) for a connection to an alternative external energy or data source. Matrix router (200) may further comprise additional buttons or other features for switching between energy or data sources, in the same manner as the interface button (205) shown in of FIGS. 2A and 3A allows switching between multiple handpieces. Indeed, in some embodiments, there might be only a single interface port (201), which may allow multiple pieces of equipment, such as different generators, to drive a single disposable device, such as a transpolar pen. In one embodiment, a foot switch (not shown) is coupled with the matrix router (200) to initiate delivery of RF energy as an example. Such a foot switch could be used to substitute or supplement the interface button (205), the mode button (204), and/or provide any other suitable features. In yet another embodiment, a substitute or supplement for the interface button (205) and/or the mode button (204) is provided in a surgical device (not shown) coupled with the matrix router (200). In this embodiment, the matrix router (200) is operable to detect selections made by such a feature on the surgical device, and is configured to provide a signal to the surgical device in accordance with such selections.

Figure 5:
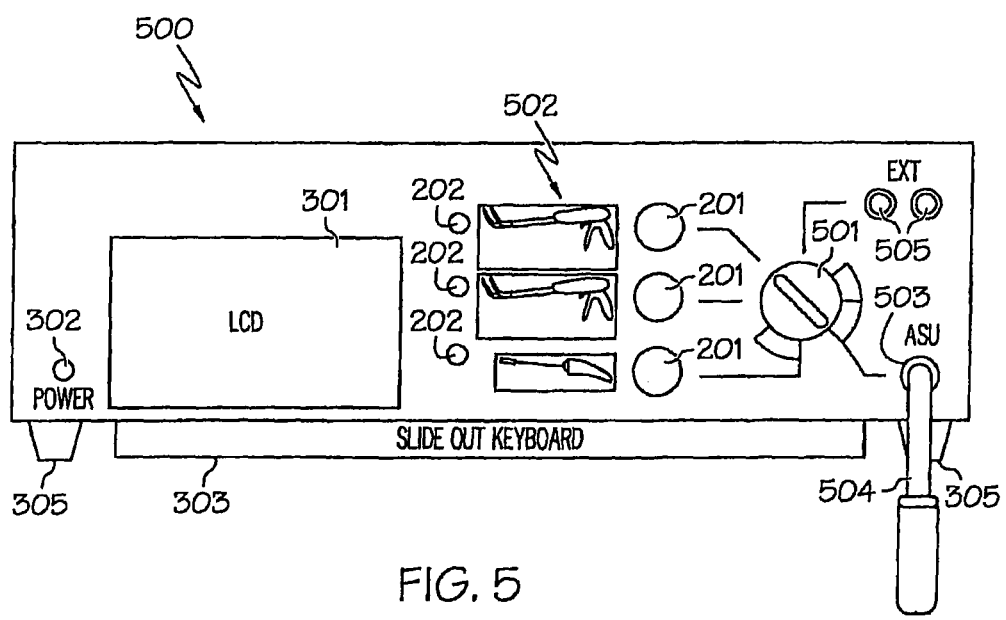
FIG. 5 illustrates a front view of a second alternative matrix router.

FIG. 5 shows a front view of another alternative matrix router (500). In this example, the interface and mode buttons (204, 205) shown in FIGS. 2A and 3A have been replaced with a single selection dial (501) which is operable to control which interface port (201) is to be connected to an ASU (not shown) or to another device. Additionally, the matrix router (500) of this example includes pictorial indications (502) of devices for each interface port (201), increasing the convenience of using the matrix router (500). The matrix router (500) further comprises an interface (503) for connecting a cable (504) to an ASU, as well as additional ports (505) for connecting an additional external power source or other external device. In this way, matrix router (500) combines the interface functionality illustrated in FIGS. 2A and 3A, with the power interface components shown in FIG. 4B.

Figure 6:
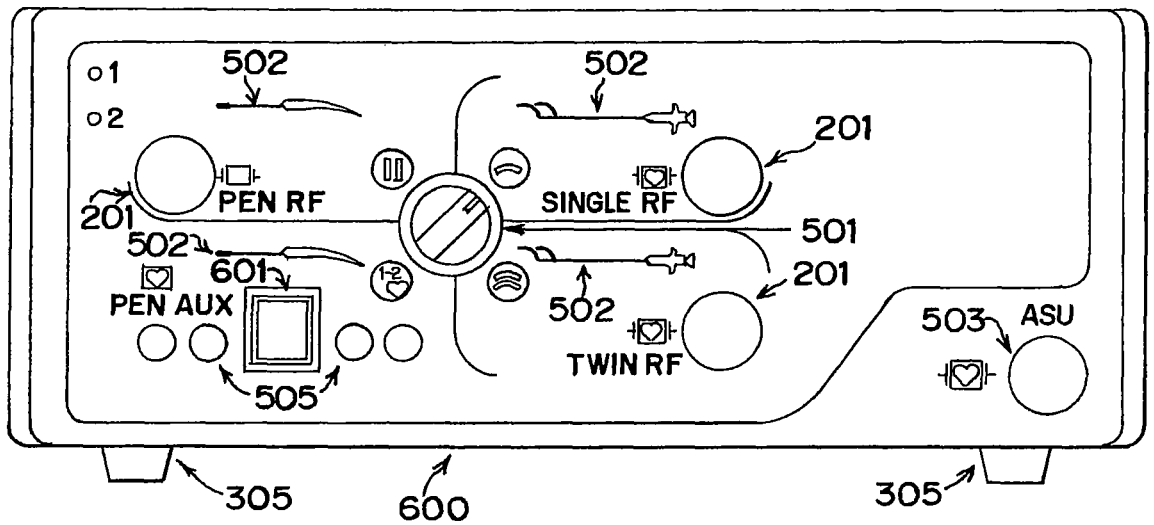
FIG. 6 illustrates a front view of a third alternative matrix router.

FIG. 6 shows a front view of another alternative matrix router (600) having many of the features described in relation to previous diagrams, such as a selection dial (501), interface ports (201), an interface (503) for connecting to an ASU, as well as other ports (505) for connecting to additional external power sources or other external devices. However, while there are similarities between the matrix router (600) depicted in FIG. 6 and those depicted previously, there are also some differences. One such difference is that, the matrix router (600) depicted in FIG. 6 includes two additional ports (505) for connecting to additional external power sources or other external devices. Those additional ports (505) could be used to simplify the performance of procedures which utilize additional pieces of external equipment. For example, in the matrix router (600) of FIG. 6, a dedicated ablation unit could be connected to the interface (503), and separate pacing and sensing units could be connected to the additional ports (505). When utilizing the pacing or sensing units, the surgeon could switch to the appropriate additional port (505) using the switch (601) between those ports (505). This might simplify workflow by allowing a surgeon to alternate between multiple pieces of additional equipment (the pacing and sensing units) by using a switch (601) rather than by disconnecting one piece of equipment so that the other could be connected to the single additional port (505). Of course, as will be apparent to one of ordinary skill in the art, the invention is not restricted to the numbers or configurations of ports depicted in the diagrams, and some embodiments of the invention will include matrix routers with more ports, or ports in alternate configurations, or both. For example, FIG. 7 depicts a matrix router (700) in which switching between additional ports (505) is performed using a selection dial (501) rather than with a dedicated switch as in FIG. 6.

Figure 7:
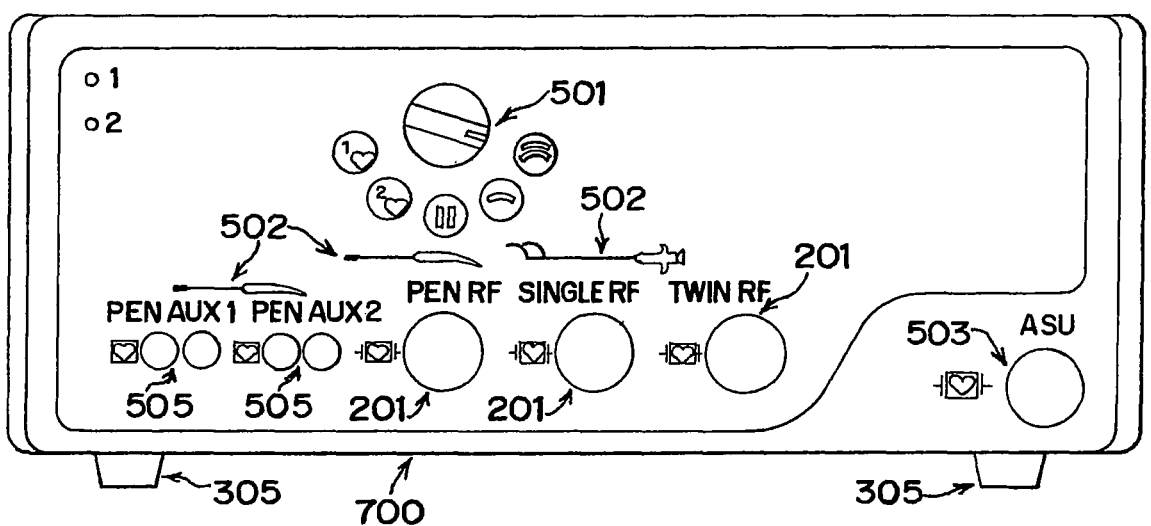
FIG. 7 illustrates a front view of a fourth alternative matrix router.

While FIGS. 5-7 demonstrate one particular alternate means of switching handpiece connections, the selection dial (501), it will be apparent to one of ordinary skill in the art that there are many additional features, such as levers, sliders, switches, etc., which could be used to select handpiece connections. Further, it will be immediately apparent to one of ordinary skill in the art that various other components, such as a modem which could be used for remote system diagnostics or data transmission, or a fax which could be used for local transmission of full disclosure, could easily be added to a matrix router (200, 300, 500, 600, 700) and that such augmented matrix routers are well within the scope of the invention. Further, one of ordinary skill in the art will immediately recognize that virtually any component of a matrix router (200, 300, 500, 600, 700) could be integrated into the matrix router (200, 300, 500, 600, 700) itself, or could be attached to the matrix router (200, 300, 500, 600, 700) via an interface port. To illustrate this option, the following table sets forth component configurations for a number of embodiments, and also indicates that different embodiments might have different combinations of integrated and externally provided components.

TABLE 1

|  | Handpiece Switching Only | Handpiece Switching with External Pace Input Source | Handpiece Switching with External Pace, Sense, and Stimulate Input Sources | Handpiece Switching with External Pace, Sense, and Stimulate Input Sources plus Communication | Handpiece Switching With Integrated Pace, Sense, Stimulate Circuits | Handpiece Switching With Integrated Pace, Sense, Stimulate Circuits plus Communication |
| --- | --- | --- | --- | --- | --- | --- |
| Transpolar Clamp | E | E | E | E | E | E |
| Transpolar Pen | E | E | E | E | E | E |
| Pace Module |  | E | E | E | X | X |
| Stimulate Module |  |  | E | E | X | X |
| Patient ECG |  | E | E | E | X | X |
| Thermal Printer |  | X | X | X | X | X |
| Graphical Display/KB |  |  |  | X |  | X |
| Modem |  |  |  | X |  | X |
| Mass Storage |  |  |  | X |  | X |

E = Externally provided to the matrix router.
X = Integrated with the matrix router.

Of course, the configurations shown in Table 1 are merely exemplary. Still other ways in which features may be allocated integrally and externally will be apparent to those of ordinary skill in the art.

In addition to simplifying the use of various surgical devices as set forth above, certain embodiments of the matrix router (200, 300, 500, 600, 700) might additionally be configured to automatically document the use of the matrix router (200, 300, 500, 600, 700). For example, in some embodiments, the matrix router (200, 300, 500, 600, 700) might automatically compile a record of which interfaces and/or which modes were activated throughout the course of a surgical procedure. Similarly, in some embodiments which include data inputs, such as an ECG, the matrix router (200, 300, 500, 600, 700) might automatically compile information provided by those data inputs as well. Such data compilation might be further integrated with data provided through the keyboard, or might be used as an additional or alternative source of documentation for a surgical procedure.

One advantage accruing to the matrix router described in the present application is that switching can be configured so that one or more interface ports is active at the same time. For example, the switching can be configured so that when a transpolar clamp interface port is activated for ablation, the interface port for the transpolar pen is simultaneously activated so that the transpolar pen can be used only for, e.g., sensing or pacing (but not for ablation). Using the pen for sensing would allow monitoring the progress of ablation and the confirmation of the creation of a transmural (i.e., isolating) line of ablation in real time by means of a intracardiac recording system connected to one of the auxiliary interface ports (505) ("PSS ports"), an electrical pathway being established between the PSS port and the transpolar pen port (and an RF energy pathway to the pen being disabled) whenever a clamp port is selected.

Thus, as an example, with the selection dial activating a clamp interface port, a procedure may be performed in which an ablation clamp is located around the pulmonary veins for making an electrically isolating line of ablation. The pen is placed in contact with the heart adjacent to the clamp on the pulmonary vein side of the clamp, and a baseline reading of the cardiac (electrical) potential is taken. Ablation with the clamp commences with the pen continuing to be in contact with the cardiac tissue so as to receive, in real time as the ablation is taking place, a signal corresponding to the cardiac potential. The signal is simultaneously displayed and recorded by the recording system attached to the PSS port. Thus, confirmation of the creation of an isolating lesion can be seen in real time as the cardiac potential, measured by the pen, attenuates and vanishes with the creation of a fully transmural lesion.

Alternatively, or additionally, a pacing unit may be connected to one of the PSS ports. The transpolar pen may then be used to apply a pacing/stimulation signal to the heart at a rate different from the patient's normal heart rate. Then, by observation of a separate EKG monitor, or by observation of the patient's beating heart, transmurality of the lesion can be confirmed, in real time, by the attenuation and vanishing of the effect of the pacing signal and the resumption of the patient's normal cardiac rhythm.

The foregoing are intended to be illustrative, and not limiting, of the types of procedures that may be performed with the matrix router of the present invention in which multiple of the interface ports are simultaneously activated.

Figure 8:
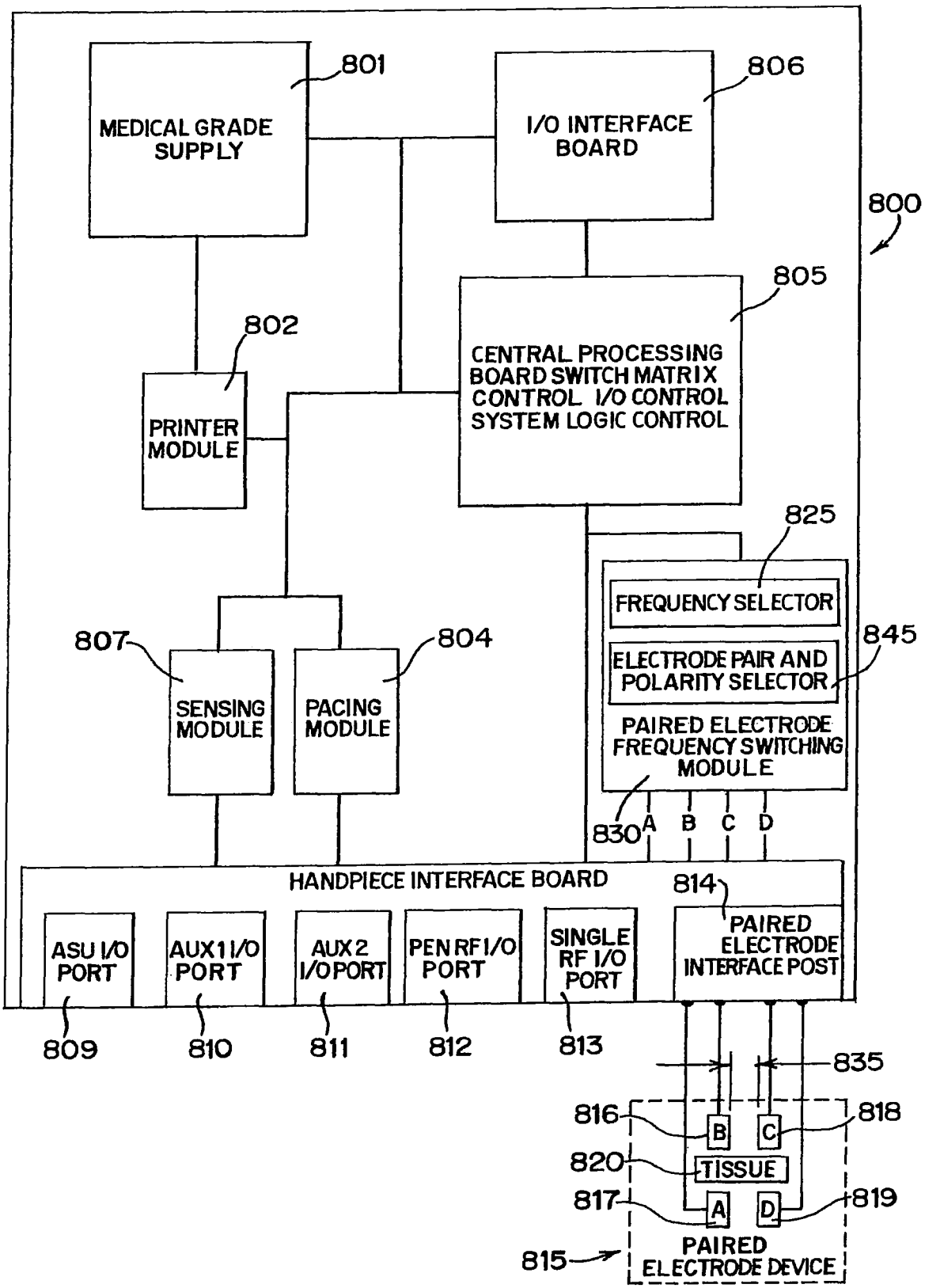
FIG. 8 is a schematic view of modules in an alternate exemplary embodiment of a matrix router with frequency switching.

FIG. 8 shows a diagram of yet another alternate embodiment, which comprises a switching matrix router (800). The switching matrix router (800) can comprise many of the features described above and shown in the previous Figs., such as an energy source (801) which can supply energy such as bipolar RF energy, a printer control module (802), a handpiece interface circuit (803), a pacing module (804), a control circuit (805), an input/output circuit (806), and a sensing module (807). For this alternate embodiment, handpiece interface board (803) can comprise a plurality of I/O ports for the connection of surgical devices to the switching matrix router (800). The plurality of I/O ports can include an ASU port (809) for connection of the ASU, an AUX 1 I/O port (810) for connection of a first auxiliary device such as a sensing or pacing unit, an AUX 2 I/O port (811) for connection of a second auxiliary device such as a sensing or pacing unit, a pen RF I/O port (812) for connection to a RF pen, a single RF I/O port (813) for the connection to a surgical device having a single pair of opposed bipolar electrodes, and a twin RF I/O port or paired electrode interface port (814). The paired electrode interface port (814) could be provided for the connection of a paired electrode device (815} to the switching matrix router (800). Such a dual paired electrode device is shown in U.S. Provisional Application No. 60/884,783, filed Jan. 12, 2007 and incorporated by reference above. The paired electrode device (815) can have at least two pairs of bipolar electrodes such as a first pair of opposed electrodes (816, 817) and a second pair of opposed electrodes (818, 819) shown opposed on opposite sides of a portion of tissue (820). The paired electrode device (815) can have one wire extending from each electrode (815, 816, 817, 818) to electrically connect the electrodes to the electrode interface port (814). The pairs of electrodes (816, 817) and (818, 819) may be opposably mounted in a clampable portion of the paired electrode device (815), such as a first jaw and a second jaw, and one or both of the jaws can be moved together to clamp tissue (820) between the jaws and electrodes (816, 817) and (818, 819). Energy can be applied to the clamped tissue 820 across the first electrode pair (816, 817) and across the second electrode pair (818, 819). The application of energy such as bipolar RF energy to the clamped tissue (820) can cauterize the clamped tissue.

In FIG. 8, the paired electrode device (815) is shown as having the electrodes (816, 817, 818, 819) spaced on two sides of the tissue (820). The electrode pairs (816, 817) and (818, 819) can be spaced apart an amount such as space (835), and, by way of example, the electrode pairs could be located parallel to one another.

Whereas the above description describes the application of energy across the first pair of opposed electrodes (816, 817) and across the second pair of opposed electrodes (818, 819), one or more additional pairs of electrodes spaced from the first and second pairs may be provided, with energy being selectively applied to tissue through the additional electrode pairs.

More specifically, the paired electrode device (815) can have "n"-number of pairs of opposed electrodes, where "n" is a number or integer that is two or greater, such as 2, 3, 4, . . . or more. For such an electrode configuration, the paired electrode interface port (814) can have a like number of electrical connections for each of the "n"-number of pairs. The selection of the electrode pairs can be electrical, mechanical, or any combination thereof. For example, an electrical circuit such as the electrode pair selector (845) could be operably coupled to the paired electrode interface port (814) to select any desired combination of paired electrodes. This selector (845) can be operator selected, an automatic selection, a pre-set selection, or pre-programmed selection. Selection can also occur anywhere, for example, by having the electrode pair selector (845) in the switching matrix router (800) or in the surgical device such as paired electrode device (815). This electrode pair selector (845) could, in one embodiment, be a circuit that can recognize a surgical device such as the paired electrode device (815) and select an appropriate combination of pairs of electrodes for that device. The electrode pair selector (845) can be located, for example, anywhere between the electrodes and the power supply (801), including, but not limited to, on the handpiece, the connector, and the box for the router. The electrode pair and polarity selector (845) can also be mechanical, electrical or electromechanical such as a switch, a connector, or a jumper. For example, the electrode pair selector (845) could be as simple as an electrical connector on the ends of a plurality of electrode wires extending from the paired electrode device (815) and electrode selection can be the order in which they are plugged into a plurality of mating 1/0 connectors in the electrode interface port (814). Thus, for example, simply unplugging one combination of the electrode wires from the fixed connectors in the paired electrode interface port (814), and re-plugging different electrode wires into different connectors in the paired electrode interface port (814) can select new electrode pair combinations. Other combinations of four wires and four connectors can be selected for different electrode configurations for the electrode pair selector (845), however the selector (845) is not limited to that particular embodiment.

A module or paired electrode frequency switching device (830) can be electrically connected between the energy source (801) and the paired electrode interface port (814), and can operate with any connected embodiment of the paired electrode device (815) described above. When the paired electrode device (815) is connected to the paired electrode interface port (814), and energy is supplied from the energy source (801), the frequency switching module (830) may rapidly alternate or switch delivery of energy such as bipolar RF energy back and forth between any selected combination of electrode pairs and polarities at a switching frequency. With a paired electrode device (815) shown having two pairs of opposed electrodes, the alternating delivery of energy at a switch[ng frequency can be timed to energize only one electrode pair at a time. As the electrode pairs are switched, the switching from the first pair to the second pair may be about instantaneous or near instantaneous. Alternately, by way of example, a slight pause or delay in the delivery of energy to the electrodes could occur slightly before the electrode pair switch, and/or during the switch, and/or slightly after the electrode pair switch. This delay between switching, for example, could be about 150 μseconds. Alternately, by way of example, whenever the paired electrode frequency switching module (830) is actuated or energy is being delivered, delivery of RF energy can be ensured to at least one pair of the selected electrode pairs such as pairs (816, 817) and (818, 819). In another alternate embodiment, the paired electrode frequency switching module (830) can prevent simultaneous power delivery to all electrode pairs.

In a further embodiment, the frequency switching matrix router (800) and/or switching module (830) can contain internal circuitry and logic to meet the switching needs of any embodiment described, or switching can be driven or controlled by an external device such as, but not limited to, the ASU. An ASU port (809) is provided to deliver power or signal from the ASU to the frequency switching module (830) and/or paired electrode device (815).

The paired electrode frequency switching module (830) may provide any one or any combination of switching frequencies. The appropriate frequency for a paired electrode device (815) can be selected as a function of surgical device and/or system parameters. These surgical device parameters can include, but are not limited to: spacing of the electrode pairs (816, 817) and (818, 819), the length of the electrodes, the RF power level with respect to tissue impedance, and the spring rate/compression force of the jaws holding the electrode pairs clamped on tissue. Selection of the appropriate frequency can be accomplished in a variety of ways through a frequency selector (818), which can be a manual switch such as a dial switch, a dip switch, jumpers, or a paired electrode device (815) recognition circuit using logic and/or surgical device recognition within the switching matrix router (800) or ASU. For example, the frequency selector (825) can identify the paired electrode device (815) and can select a switching frequency for that specific device. Such recognition could occur when the surgical device such as the paired electrode device (815) is electrically connected to the paired electrode interface port (814), and both device detection and frequency selection can be driven by the switching matrix router (800) or by the ASU. Alternately, the frequency selector (818) can be a portion of a surgical device such as paired electrode device (815).

Switching frequencies of the frequency switching module (830) can be between but are not limited to about 2 Hz and about 575 Hz. In another example, a frequency for a surgical device can range between 10 Hz to about 376 Hz. Alternately, in yet another embodiment, the frequency or a frequency range can be any selected from TABLE 2.

TABLE 2

| Switching Frequency Selections (Hz) | | |
|---|---|---|
| Selection No. | Nominal frequency | Frequency Range |
| 1 | 523 | 471-575 |
| 2 | 467 | 421-513 |
| 3 | 417 | 376-456 |
| 4 | 367 | 331-403 |
| 5 | 337 | 304-370 |
| 6 | 267 | 241-293 |
| 7 | 213 | 192-234 |
| 8 | 157 | 142-173 |
| 9 | 113 | 102-124 |
| 10 | 77 | 70-84 |
| 11 | 53 | 48-58 |
| 12 | 43 | 39-47 |
| 13 | 33 | 30-36 |
| 14 | 27 | 25-29 |
| 15 | 21 | 19-23 |
| 16 | 11 | 10-12 |
| 17 | 5 | 1-9 |

In addition to controlling and selecting the frequency, the paired electrode frequency shifting device (830) can be used to control the duty cycle for at least one of the pairs of the opposed electrodes. In an example, the paired electrode frequency shifting device (830) can alternate the energy between the respective pairs of electrodes at a duty cycle of less than 100% for each pair of electrodes.

Alternately, from a system level, the paired electrode frequency switching device (830) can be placed at any point between the energy source (801), and the paired electrodes such as the first pair of opposed electrodes (816, 817) and the second pair of opposed electrodes (818, 819).

While the matrix router and surgical device have been described as a utilizing bipolar RF energy, other energy sources may be utilized such as ultrasonic energy, mono-polar radio frequency energy, microwave energy, laser energy, or other types of energy. The surgical device can have n-number of paired (for bipolar application) or individual (for unipolar application) sets of ablation energy delivery surfaces (such as electrodes when, e.g., RF energy is used) where n is greater than 2, and each electrode pair or active surface can cauterize tissue clamped therebetween or placed thereupon with any of the energies described above. In an embodiment, the alternate frequency switching matrix router can include a switching module that can alternate delivery of any energy to the n-numbered paired energy delivery surfaces of the alternate surgical device.

As described above, the matrix router includes an interface button (205) or a selection dial (501) on the front panel for establishing a connection between the energy generator and the desired interface ports (e.g. interface ports (201) and (505)). In a typical operating room, access to the front panel of the matrix router to manipulate the interface buttons/selection dial may be impeded due to limited space for personnel within the sterile field. Accordingly, in keeping with another aspect of the invention, the matrix router may be provided with a second interface button/selection dial on the rear panel that is operatively connected to the button/dial on the front panel. This permits the button/dial to be manipulated from either the front or rear panel to selectively connect the desired interface ports to the energy generator or other peripheral devices.

Figure 9:
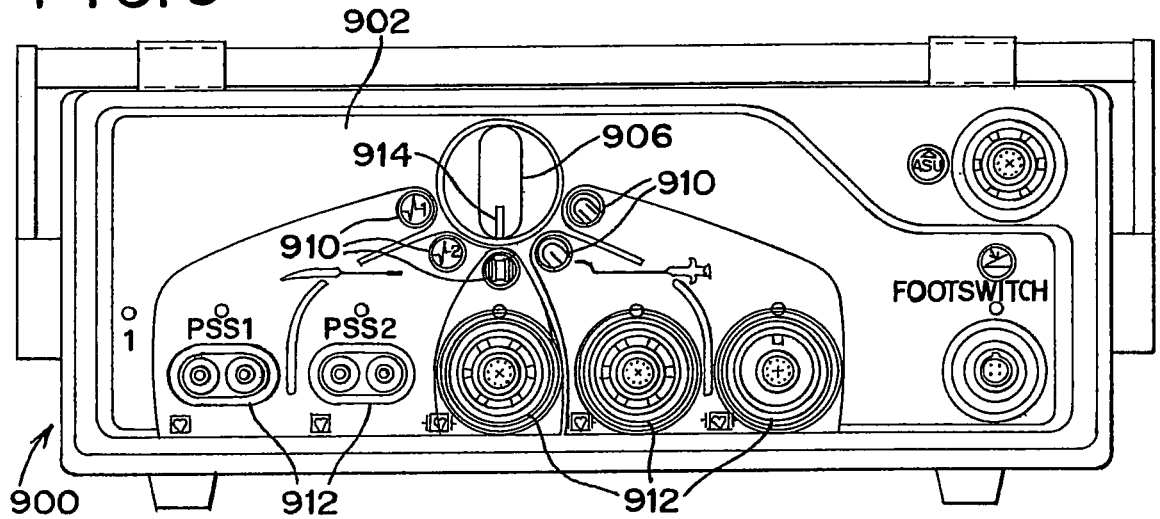
FIGS. 9 and 10 illustrate a front panel and rear panel, respectively, of a fifth alternative matrix router.
Figure 10:
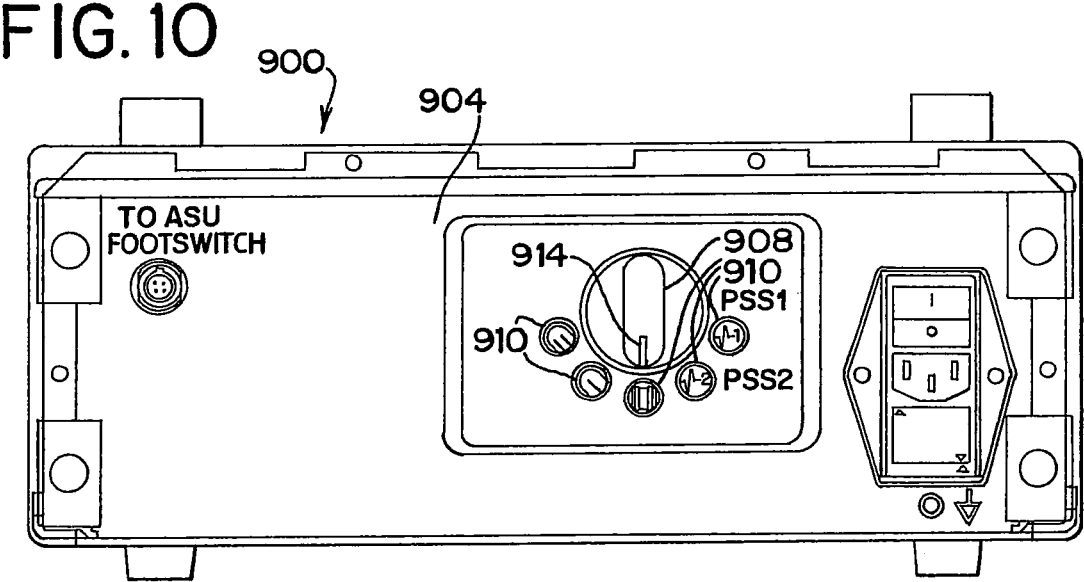

With reference to FIGS. 9 and 10, the front and rear panels (902, 904, respectively), of a matrix router (900) are shown, each having a selection dial ((906) for the front panel and (908) for the rear panel). The selection dials (906, 908) are operatively connected so that they operate in tandem, regardless of whether the port selection is made with the selection dial (906) on the front panel (902) or the selection dial (908) on the rear panel (904). The front and rear panels (902, 904) also have markings or other visual indications of the interface port or ports (912) that are selected. The visual indication may be in the form of graphics on the panel and a pointer (914) on the selection dial (906, 908), as is shown in the illustrated. embodiment. Other visual indicators are also contemplated, such as lights. Regardless, the same visual indication is provided to a person viewing the rear panel as is provided to a person viewing the front panel.

Figure 11:
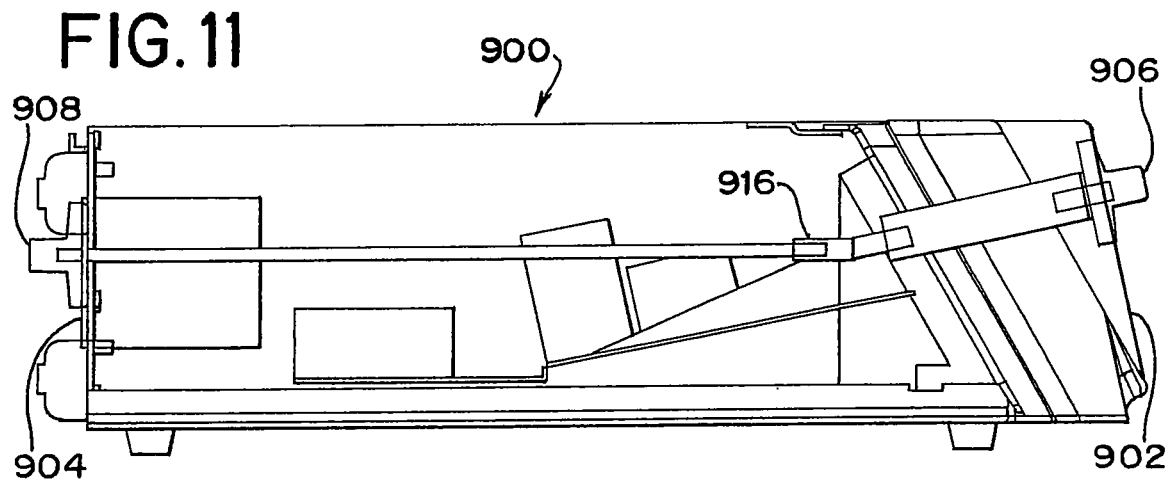
FIG. 11 is a cross-sectional view of the matrix router of FIGS. 9 and 10.

The operative connection between the buttons/dials on the front panel and the rear panels may be mechanical, such as through an articulated linkage (916) directly connecting the front dial (906) and the rear dial (908) (as shown in FIG. 11). Alternatively, the front and rear selectors may be connected electronically. The port selection may also be controlled by a remote control handpiece.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

What is claimed is:

1. A surgical router for connecting one or more surgical devices thereto that include a paired electrode device including at least a first pair of opposed electrodes and a second pair of opposed electrodes for clamping and cauterizing tissue therebetween, the surgical router comprising:
   a) an energy source;
   b) an interface port, operably connected to the energy source, comprising a paired electrode interface port for connecting the paired electrode device thereto; and
   c) a switching device operably connected between the energy source and the paired electrode interface port, wherein the switching device is configured to rapidly alternate delivery of energy back and forth between the first pair of opposed electrodes and the second pair of opposed electrodes.

2. The surgical router of claim 1, wherein:
   the switching device is configured to rapidly alternate delivery of energy back and forth between the first pair of opposed electrodes and the second pair of opposed electrodes at a switching frequency; and,
   the switching frequency of the switching device is selected with a frequency selector.

3. The surgical router of claim 2, wherein the frequency selector is at least one switch.

4. The surgical router of claim 2, wherein the frequency selector is at least one jumper.

5. The surgical router of claim 2, wherein the frequency selector is in the paired electrode device.

6. The surgical router of claim 2, wherein the frequency selector is a circuit that recognizes any one of a plurality of paired electrode devices and can select a frequency for any one of the paired electrode devices.

7. The surgical router of claim 2, wherein the frequency selector selects a switching frequency as a function of a spacing between the each pair of opposed electrodes of the paired electrode device.

8. The surgical router of claim 2, wherein the frequency selector selects a switching frequency as a function of the length of the electrodes of the paired electrode device.

9. The surgical router of claim 1 wherein a member of each pair of opposed electrodes is located in one jaw of a pair of clampable jaws and the switching frequency selected by the frequency selector is a function of an RF energy power level with respect to an impedance of the tissue clamped between the each pair of opposed electrodes.

10. The surgical router of claim 2, wherein when the first pair of opposed electrodes and the second pair of opposed electrodes of the paired electrode device are clamped on tissue, the frequency selector selects a switching frequency as a function of an energy power level provided by the energy source with respect to an impedance measured across the tissue clamped between the pairs of opposed electrodes.

11. The surgical router of claim 2, wherein a member of each pair of opposed electrodes are located in one jaw of a pair of clampable jaws and the switching frequency selected by the frequency selector is a function of a spring rate and the clamp pressure exerted on the tissue clamped between by the clampable jaws.

12. The surgical router of claim 2, wherein when the first pair of opposed electrodes and the second pair of opposed electrodes of the paired electrode device are clamped on tissue, the switching frequency selected by the frequency selector is a function of a spring rate of portions of the paired electrode device that both mount the opposed electrode pairs and exert a clamping pressure onto the tissue.

13. The surgical router of claim 1, wherein any combination of the electrode pairs can be selected for the paired electrode device.

14. The surgical router of claim 1, wherein when energy is being delivered, the switching device prevents energy from being about simultaneously delivered to each respective pair of opposed electrodes of the paired electrode device.

15. The surgical router of claim 1, wherein when energy is being switched among the first pair of opposed electrodes and the second pair of opposed electrodes, energy delivery can be delayed from about just before a switch to just after a switch.

16. The surgical router of claim 1, wherein energy is delivered at any given time during activation of the router, to at least one pair of opposed electrodes of the paired electrode device.

17. The surgical system of claim 1 wherein the switching device alternates the energy between the respective pairs of electrodes at a duty cycle of less than 100% for each pair.

18. The surgical router of claim 1, wherein the switching frequency is between about 10 Hz and about 376 Hz.

19. A switch box for selectively electrically connecting a medical device to a power source, the switch box comprising:

a paired electrode interface port adapted for physically connecting the medical device to the switch box;

a switching module configured to rapidly alternate back and forth delivery of energy to the paired electrode interface port when the switch box is electrically connected to the power source.

20. A switch box for selectively electrically connecting one or more medical devices to a power source, the switch box comprising:

at least three input ports adapted for physically connecting the one or more medical devices to the switch box;

an actuator configured to simultaneously: (i) switch a first of the at least three input ports into electrical communication with power source, (ii) switch a second of the at least three input ports into electrical communication with the power source, and (iii) switch a third of the at least three input ports to discontinue electrical communication with the power source.

* * * * *